United States Patent

Davis

[11] Patent Number: 5,882,600
[45] Date of Patent: *Mar. 16, 1999

[54] LID FOR AN ANALYTICAL SPECIMEN CUP

[75] Inventor: Richard C. Davis, Tampa, Fla.

[73] Assignee: Urocath Corporation, Tampa, Fla.

[ * ] Notice: The term of this patent shall not extend beyond the expiration date of Pat. No. 5,640,969.

[21] Appl. No.: 832,188

[22] Filed: Apr. 8, 1997

Related U.S. Application Data

[62] Division of Ser. No. 441,917, May 16, 1995, Pat. No. 5,640,969.

[51] Int. Cl.$^6$ .............................. B01L 3/00; A61B 5/00
[52] U.S. Cl. ........................... 422/102; 422/58; 128/771; 128/760; 604/317; 604/403
[58] Field of Search .................... 422/56, 58, 102, 422/104; 128/771, 760; 604/317, 318, 403, 404

[56] References Cited

U.S. PATENT DOCUMENTS

| | | | |
|---|---|---|---|
| 3,774,455 | 11/1973 | Seidler et al. | 73/444 |
| 3,924,741 | 12/1975 | Kachur et al. | 206/221 |
| 4,024,952 | 5/1977 | Leitz | 206/221 |
| 4,092,120 | 5/1978 | Suovaniemi et al. | 422/58 |
| 4,109,530 | 8/1978 | Kim | 73/427 |
| 4,225,557 | 9/1980 | Hartl et al. | 422/56 |
| 4,573,580 | 3/1986 | Messer | 206/534 |
| 4,827,944 | 5/1989 | Nugent | 128/771 |
| 4,869,398 | 9/1989 | Colvin et al. | 222/83 |
| 4,912,034 | 3/1990 | Kalra et al. | 435/7 |
| 5,086,913 | 2/1992 | Camm et al. | 206/5.1 |
| 5,106,758 | 4/1992 | Adler et al. | 436/165 |
| 5,119,830 | 6/1992 | Davis | 128/771 |
| 5,403,551 | 4/1995 | Galloway et al. | 422/58 |
| 5,429,804 | 7/1995 | Sayles | 422/58 |
| 5,496,736 | 3/1996 | Stone | 436/81 |
| 5,501,837 | 3/1996 | Sayles | 422/58 |
| 5,518,003 | 5/1996 | Allan | 128/761 |
| 5,591,401 | 1/1997 | Sayles | 422/58 |
| 5,726,010 | 3/1998 | Clark | 435/5 |
| 5,726,013 | 3/1998 | Clark | 435/5 |

Primary Examiner—Harold Y. Pyon
Attorney, Agent, or Firm—Griffin, Butler Whisenhunt & Szipl, LLP

[57] ABSTRACT

A removable lid (10) for an analytical specimen cup (12) of a type for defining a test space (26) with a chemical strip (24) mounted therein includes a selectively-removable protective cover (16) for selectively covering and uncovering an outer surface of a transparent portion of an outer partition (18) forming the test space. The protective cover is formed as one piece with an inner partition to be attached thereto by a dual living hinge (28a and b). The lid is rectangular in shape and includes an elongated magnifying lens (20) which has protrusions extending into blind holes (62) of the inner partition. The magnifying lens extends across the transparent portion of the outer partition. When the protective cover is in a closed position it impinges on the magnifying lens. A peel-off color analysis chart (22) is mounted on an inside surface of the protective cover.

4 Claims, 2 Drawing Sheets

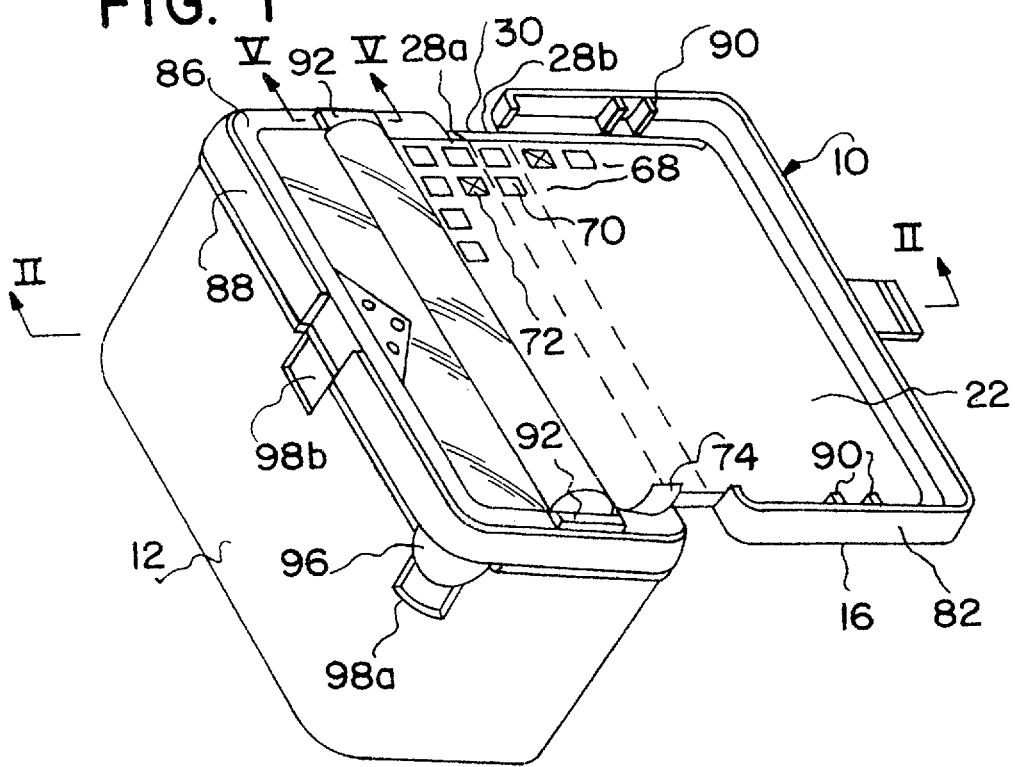
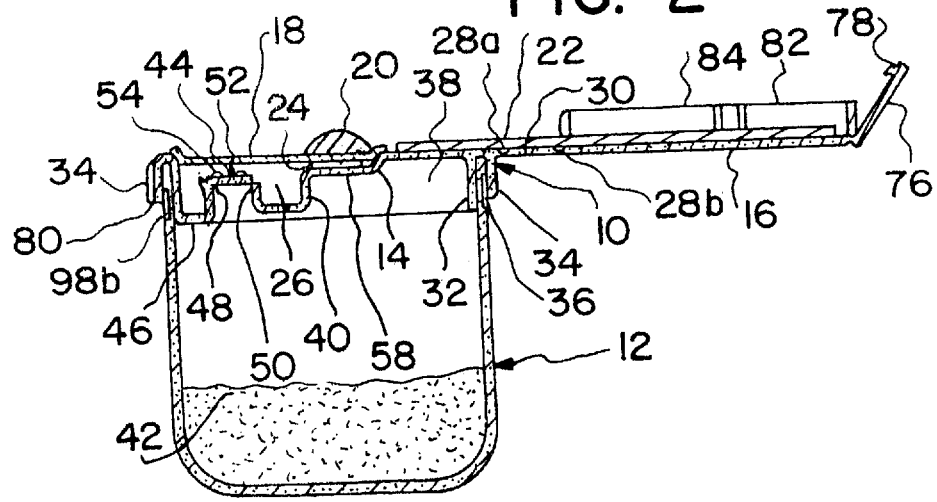

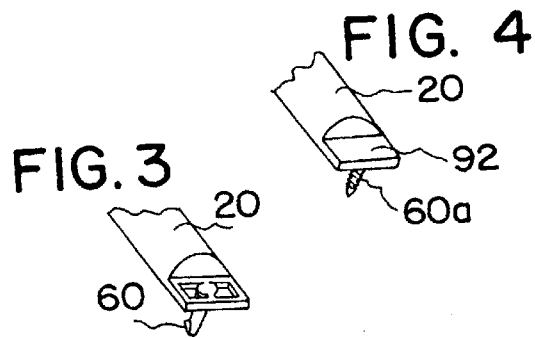
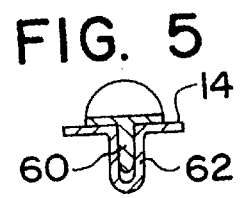
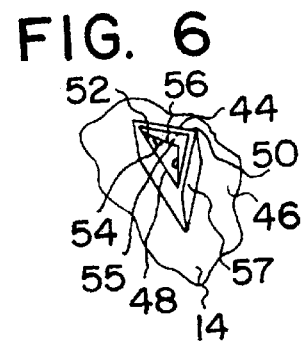
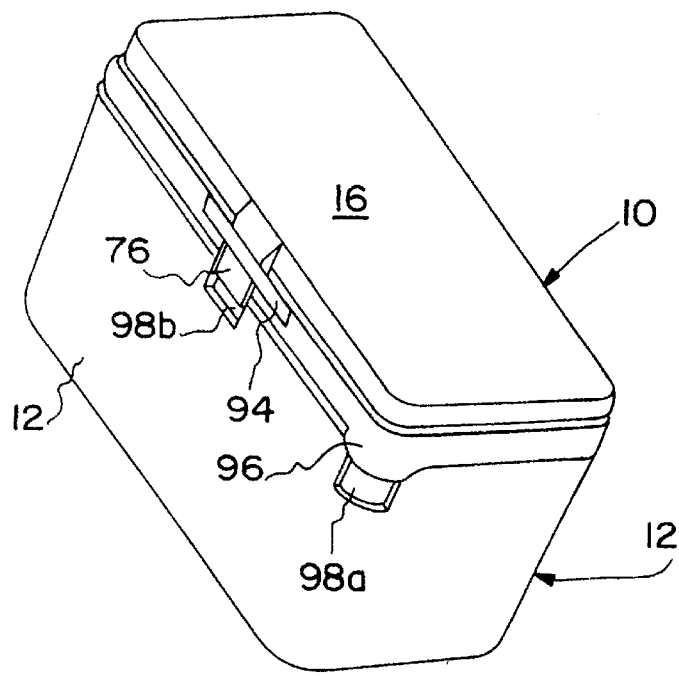

LID FOR AN ANALYTICAL SPECIMEN CUP

This application is a divisional application of U.S. application Ser. No. 80/441,917, filed May 16, 1995, now U.S. Pat. No. 5,640,969

BACKGROUND OF THE INVENTION

This invention relates generally to specimen cup lids, chemical test strips for analyzing contents of analytical specimen cups, and, specifically, to analytical specimen cup lids which are combined with chemical test strips.

It has been suggested to combine chemical test strips with analytical specimen cup lids so that contents of specimen cups on which the lids are mounted can be analyzed without the necessity of opening the specimen cups and inserting chemical strips therein.

For example, U.S. Pat. No. 5,119,830 to Davis describes an analytical specimen cup lid coupled with a test strip. That is, an analytical specimen cup has a lid with outer and inner partitions to define a test space therebetween in which a chemical test strip is mounted. A fluid specimen in the cup is selectively introduced to the chemical strip in the test space by manipulating a frangible valve which breaks an opening in the inner partition. Thus, the analytical specimen cup described in U.S. Pat. No. 5,119,830 to Davis allows technicians to control when fluid specimen is introduced to a chemical test strip so that the technicians need do this only when they are prepared to read and record data.

U.S. patent application Ser. No. 08/262,535, filed Jun. 20, 1994 by Davis discloses the concept of placing the chemical test strip on a raised shelf in the test space so that the chemical test strip does not remain in contact with a specimen introduced into the test space. Davis also discloses therein the placement of a peel-off color-analysis chart on an exterior surface of the lid adjacent the chemical test strip so that the peel-off color-analysis chart can be easily compared with the chemical test strip, appropriately marked, peeled from the lid, and placed on a patient's chart. Although this device has various beneficial structures, it still has several shortcomings. One problem with this device is that an exposed unprotected lid of this design could be damaged in storage or transport, tampered with, or have a hole poked in a transparent portion of the outer partition, thereby making the lid virtually unusable.

For this reason, it is an object of this invention to provide a lid for an analytical specimen cup of a type providing a test space with a chemical strip therein which is more safely transported and stored and which is relatively tamper proof.

Yet another difficulty with devices of the prior art described above is that they allow light and moisture to continually enter the test space and thereby adversely affect the chemical strip therein. In this regard, it is desirably that chemical test patches be protected from light, especially sunlight, and moisture because such influences tend to discolor chemical patches on chemical test strips and, therefore, make "readings" taken from the test strips inaccurate.

Thus, it is a further object of this invention to provide a lid for an analytical specimen cup of a type defining a test space with a transparent partition which does not normally allow an undue amount of light and/or moisture to reach a chemical strip in the test space.

Yet another difficulty with some of the prior art devices described above is that they suggest the use of an optical magnifying lens as part of a lid for aiding a technician in reading the chemical test strip, but they do not suggest a practical manner of incorporating such a magnifying lens into the lid. Therefore, it is an object of this invention to provide a lid for an analytical specimen cup of a type defining a test space with a chemical test strip therein having a magnifying lens incorporated therein in an inexpensive and practical manner.

It is a further object of this invention to provide a lid for an analytical specimen cup of a type defining a test space with a chemical test strip therein which is not unduly expensive to manufacture and which is uncomplicated for both patients and technicians to use.

SUMMARY OF THE INVENTION

According to principles of this invention, a lid for an analytical specimen cup of a type defining a test space with a chemical test strip therein, includes a selectively movable protective cover for selectively covering and uncovering a transparent portion of an outer partition defining the test space. The protective cover includes a fastener for holding the protective cover in a covering position, even when the lid is removed from an analytical specimen cup.

The lid is substantially rectangular in shape and includes an elongated magnifying lens having protrusions, or spikes, thereon inserted into blind holes in the lid and extending across the transparent portion of the outer partition. The lens is impinged on by the protective cover when the protective cover is in a closed position. A peel-off color-analysis chart is on an inside surface of the protective cover.

BRIEF DESCRIPTION OF THE DRAWING

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 1 is an isometric view of a removable lid of this invention mounted on an analytical specimen cup with a protective cover of the removable lid being in an open position;

FIG. 2 is a cross-sectional view taken on line II—II in FIG. 1;

FIG. 3 is a segmented isometric view of a portion of a first embodiment magnetic lens of the removable lid of FIGS. 1 and 2;

FIG. 4 is a segmented isometric view of a portion of a second embodiment magnetic lens of the removable lid of FIGS. 1 and 2;

FIG. 5 is a segmented cross-sectional view taken on line IV—IV in FIG. 1;

FIG. 6 is a segmented isometric view of a specimen release device of the removable lid of FIG. 1, shown releasing specimen from the analytical specimen cup of FIG. 1; and FIG. 7 is an isometric view of the structure of FIGS. 1 and 2 with the protective cover being in a covering and latched position.

DESCRIPTION OF THE PREFERRED EMBODIMENT

A removable lid 10, which is pressed onto a specimen cup 12, basically comprises an inner partition 14, a selectively removable protective cover 16, a transparent outer partition 18, a magnifying lens 20, a peel-off color-analysis chart 22 and a chemical test strip 24 mounted in a test space 26 formed between the transparent outer partition 18 and the inner partition 14. The inner partition 14 and the protective cover 16 are molded of one piece of resinous plastic, with the protective cover 16 being contiguous to the inner partition 14, and being attached thereto by a dual living hinge 28a and 28b. A spacer 30 between hinge elements 28a and b is also molded as one piece with the inner partition 14 and the protective cover 16 and allows the protective cover 16 to be spaced from the inner partition 14 when the protective cover 16 is folded over the inner partition 14 as is shown in FIG. 7.

An inner wall 32 and an outer wall 34 form a specimen-cup receiving slot 36 at a bottom surface of the inner partition 14 extending about a periphery of the inner partition 14 for receiving an upper edge of the specimen cup 12. Thus, the removable lid 10 can be firmly seated at a mouth of the specimen cup 12 so as to cover the mouth with the inner partition 14, but can also be easily removed therefrom.

The inner partition 14 extends down into the mouth 38 of the specimen cup 12 to form a sump 40 above a specimen 42 in the specimen cup 12. A specimen release device 44, also molded as one piece with the inner partition 14, extends upwardly from a floor 46 of the sump 40 and is attached to the floor 46 by a living hinge 48 at one edge and a frangible apex 50 at two other edges. In this regard, it can be seen in FIG. 6 that the specimen release device 44 is triangular in shape so that when a force is applied to a top wall 52, having pips 54 thereon, the top wall 52 rotates at the living hinge 48 and applies great pressure at the frangible apex 50 so that a frangible connection on the specimen release device 44 breaks, with an edge 56 of the top wall 52 moving below the frangible apex 50 and creating an opening 55 through which specimen 42 can pass from the interior of the specimen cup 12 into the test space 26. The vertical wall 57 of the specimen release device 44 then serves as a snorkel to prevent more specimen 42 than is necessary from entering the test space 26.

A raised shelf 58 is formed by the inner partition 14 above the floor 46 of the sump 40 for holding the chemical test strip 24 above the floor 46. The raised shelf 48 is located at a higher level than the frangible apex 50. This position allows the specimen fluid 42 to contact the test strip 24 when the device is inverted.

The transparent outer partition 18 is formed of a separate member which is adhered to the inner partition 14. In this regard, the transparent outer partition 18, in a preferred embodiment, is formed of an extruded multi-laminate film or of a single ply plastic film, such as mylar or maybe of other materials which may be adhered, glued, heat-sealed, RF sealed or otherwise sealably connected to the surface of the inner partition 14, so as to enclose the test space 26. As can be seen in FIG. 2, the top surface 52 of the specimen release device is immediately below the transparent outer partition 18. In a preferred embodiment, the inner partition 14 and the protective cover 16, along with the dual living hinges 28a and b and spacer 30 and other attached components are molded as one piece of polypropylene or of another suitable flexible resinous plastic.

The magnifying lens 20 is formed as a separate piece of a polycarbonate plastic such as LAXAN sold by 3M. The magnifying lens 20 is attached to the inner partition 14 by means of protrusions, or spikes, 60 formed at opposite ends of the magnifying lens 20 which extend into blind holes 62 (holes which do not extend completely through) in the inner partition 14, as is shown in FIG. 5. In this regard, the protrusion 60, 60a can have barbs thereon for holding more tightly in the blind holes 62 and, in a preferred embodiment, walls forming the blind holes 62 are hexagonal in shape so as to allow some flexibility for receiving the cylindrically shaped protrusions 60, 60a as they are inserted therein, but yet to also tightly hold the protrusions. Once the magnifying lens 20 is mounted on the inner partition 14 in this manner, it stiffens the inner partition 14 and, thereby, stiffens the entire rectangular removable lid 10. As can be seen in FIG. 2, when the magnifying lens 20 is mounted on the inner partition 14, it extends above and across the transparent outer partition 18 as well as the chemical test strip 24, which is mounted on the raised shelf 58 of the inner partition 14. It is also noted that the space between the transparent outer partition 18 and the surface of the chemical test strip 24 is sufficiently large to prevent unwanted capillary adherence of specimen fluid 42 therebetween.

The chemical test strip 24 comprises a line of chemical patches (not shown) each of which changes to a degree of color indicative of a characteristic of the specimen 42. In this regard, for example, one of the patches will change to a particular color, or shade of color depending upon a pH level of the specimen 42 when it is contacted by the specimen 42.

The color-analysis chart 22, or label, is releasably adhered to the inner partition 14 and the protective cover 16, and thereby extends across the dual living hinge 28a and b and the spacer 30. The color-analysis chart 22 is positioned adjacent to the chemical test strip 24. The color analysis chart 22 has lines 68 of color blocks 70 thereon, each line corresponding to one of the chemical patches (not shown) on the chemical test strip 24. Each of the color blocks 70 in a line 68 has a color which is representative of a possible color that its respective chemical patch can obtain when it is contacted by the specimen 42 (one row of color blocks is positioned on the spacer 30). A technician places a cross 72 on the color block 70 most closely representing the color of its associated chemical patch. The same is repeated for each line 68 of the color blocks 70 for each of the chemical patches to respectively indicate the pH level, protein, ketone, etc. The peel-off color analysis chart 22 is then removed from the removable lid 10 by means of a tab 74 and placed onto a separate permanent record (not shown) to document the test.

As previously mentioned, the protective cover 16 can be in an open attitude, as is depicted in FIGS. 1 and 2, and in a closed attitude, as is depicted in FIG. 7. The protective cover 16 can be rotated between these two positions about the dual living hinge 28a and b. When the protective cover 16 is in the open position, the transparent outer partition 18, the specimen release device 44, the color analysis chart 22 and the magnifying lens 20 are fully exposed for use by technicians. However, when the protective cover 16 is in the closed position the transparent outer partition 18, the specimen release device 44, the color analysis chart 22 and the magnifying lens 20 are covered up, and thereby protected from tampering, storage and transport hazards, and other inadvertent damage. The protective cover 16 is retained in a closed position by means of a latch 76, which is molded as one piece with the protective cover 16 and which has a dove-tail hook 78 for engaging a lower edge 80 of the outer wall 34 for thereby holding the protective cover 16 in a closed position.

A spacer border 82 is molded as one piece with the protective cover 16 on an inner surface thereof, about three edges. When the protective cover is in the closed position shown in FIG. 7 an edge 84 of the spacer border 82 impinges on an upper surface 86 of a periphery 88 of the inner partition 14. The spacer border 82 has ribs 90 thereon which impinge on flanges 92 formed as one piece with the magnifying lens 20 to hold the magnifying lens 20 in a proper position with its protrusions 60, 60a seated.

When the protective cover 16 is in the closed position shown in FIG. 7 it can have a tamper indicator/seal 94 extending across the latch 76 to ensure that the protective cover 16 remains latched, or locked, to the inner partition 14. It should be understood that when the protective cover 16 is thusly locked to the inner partition 14, the entire removable lid 10 can be removed from the specimen cup 12 without exposing the transparent outer partition 18, the specimen release device 44, the color analysis chart 22 and the magnifying lens 20 to tampering. Further, the indicator seal 94 will show technicians if anyone has tampered with the removable lid 10.

Further embellishments of this invention include lid removal tabs 96 at opposite corners of the outer wall 34 of the inner partition 14 and indentations 98a in the specimen cup 12 at opposite corners thereof to facilitate users removing the removable lid 10 from the specimen cup 12. The indentations 98a make it easier to grip the lid removable tab 96. Also, in one embodiment, indentations 98b are included in the center of opposite outer surfaces of the specimen cup 12 to make it easier for a technician to grip the latch 76.

Looking now at overall operation of the removable lid 10 and its companion specimen cup 12, the removable lid 10 and the specimen cup 12 are manufactured separately. Once the removable lid 10 has been assembled with the chemical test strip 24 mounted on the raised shelf 58, the transparent outer partition 18 is sealably affixed to the inner partition 14 so as to enclose the test space 26, the color-analysis chart 22 is adhered to the inner partition 14 and the protective cover 16, the magnifying lens 20 is mounted on the inner partition 14, the protective cover 16 is rotated about the dual living hinge 28a and b to the closed position shown in FIG. 7 (although the removable lid is not yet mounted on a specimen cup as shown in FIG. 7), and the dove-tail hook 78 of the latch 76 is placed under the lower edge 80 of the outer wall 34 to maintain the protective cover in the closed position. The seal 94 is placed across the latch 76, adhered to the outer wall 34 so as to prevent the protective cover 16 from being rotated to an open position unless the seal 94 is broken. The removable lid 10 is then forced onto a specimen cup 12 as shown in FIG. 7 (the protective cover will be in the closed position shown in FIG. 7 rather than in the open position shown in FIG. 2).

This composite specimen cup and removable lid is thusly sold to clinics, doctors, hospitals, laboratories, industries, technicians, and the like. When the specimen cup is to be used, it is given to a user and it appears, to the user, that it is merely a specimen cup with a lid. That is, the user cannot easily see that the removable lid 10 includes a sealed protective cover 16. The user removes the removable lid 10 from the specimen cup 12, deposits the specimen 42 therein, and sealably presses the removable lid 10 onto the specimen cup 12. The specimen cup 12 is maintained in this configuration, housing the specimen 42, until a technician is prepared to analyze the specimen 42.

In order to analyze the specimen 42, the technician breaks the seal 94 and detaches the latch 76 from the lower edge 80 to rotate the protective cover 16 from its covering position. The technician then forcible depresses the transparent outer partition 18 against the top surface 52 of the specimen release device 44, thereby braking the frangible apex 50 of the inner partition 14 and rotating the top wall 52 about the living hinge 48. The specimen cup 12 is then inverted so that the specimen 42 enters the test space 26 through the opening 55 at the broken frangible apex 50 into the test space 26. The specimen 42 entering the up-side-down test space 26 will come into contact with the chemical test strip 24 but the snorkel wall 57 of the specimen releasable device 44 will prevent an undue amount of specimen from entering the test space 26. The specimen cup 12 is then turned right-side-up so that specimen drains away from the chemical test strip 24 on the raised shelf 58 into the sump 40. Thus, air then comes in contact with chemical patches on the chemical test strip 24 causing them to properly react to the specimen 42. Colors achieved by the chemical patches on the chemical test strip 24 are read by a technician through the magnifying lens 20 and these colors are compared with color blocks 70 adjacent the patches. Crosses 72 are placed on corresponding color blocks 70 to indicate colors of the chemical patches on the chemical strip 24. Using the tab 74, the color-analysis chart 22 is then removed and placed in a permanent record. The specimen cup 12 and its removable lid can then be discarded or saved so that the specimen 42 can be used for further tests.

It is highly beneficial to have a removable lid covering the transparent outer partition 18, the specimen release device 44, the color analysis chart 22 and the magnifying lens 20 to ensure that the integrity of the test space 26 and the lid 10 itself have been maintained.

Similarly, it is highly advantageous that the protective cover of this invention is integrated into the removable lid in such a way that users accept the removable lid as being a normal one piece lid so that they will not try to remove the protective cover 16, and thereby inadvertently tamper with the analyzing elements of the removable lid.

It is also highly advantageous that the protective cover 16 normally blocks light and moisture from passing through the transparent outer partition 18 to the chemical strip 24, because in this way the protective cover 16 ensures that readings taken from the chemical test strip 24 are more accurate.

It is also beneficial that the inner partition 14 and the protective cover 16 can be molded of one piece of plastic joined by a living hinge because in this manner the removable lid 10 can be manufactured in a cost effective manner.

Further, it is beneficial that the specimen cup 12 and the removable lid 10 are formed in a rectangular shape and that the magnifying lens 20 is elongated. With this configuration the removable lid and the specimen cup are stable in shape. In this regard, the separate elongated magnifying lens provides stiffness to the removable lid 10.

Similarly, it is beneficial that the magnifying lens is attached to the inner partition by protrusions, or spikes, which extend into blind holes. Such an attachment is economical to manufacture and provides structural stability.

It is also beneficial that the protective cover has ribs thereon which impinge on the magnifying lens when the protective cover is in a closed position for maintaining the magnifying lens in a proper position.

Yet another beneficial aspect of this invention is that the foldable protective cover provides a larger area onto which the peel-off analysis chart can be placed, with the chart extending across the dual living hinge 28a and b, without requiring that the specimen cup be unduly large. When the protective cover 16 is folded out to the open position, the entire color-analysis chart 22 can be seen adjacent the chemical test strip 24. It can be seen in FIG. 1 that, in the depicted embodiment, one row of the color blocks 70 is spaced to fall on the spacer 30 between the dual living hinge elements 28*a* and *b*.

Yet another benefit of the removable lid of this invention is that when specimen cups having this removable lid thereon are transported and stored, one need not be overly careful that the transparent outer partition is not punctured. Thus, specimen cups with the removable lid of this invention thereon need not be specially packaged.

While the invention has been particularly shown and described with reference to a preferred embodiment, it will be understood by those of ordinary skill in the art that various changes in form and detail may be made therein without departing from the spirit and scope of the invention. For example, an instruction label could be attached to a top of the removable lid 10 when the removable lid 10 is in the closed position explaining to users and technicians how the removable lid is to be used. Also, the seal 94 could have a warning thereon that it is not to be removed except by technical personnel. In one preferred embodiment the frangible apex portion 50 is attached directly to the raised shelf 58.

The embodiments of the invention in which an exclusive property or privilege are claimed are defined as follows:

1. A removable lid for an analytical specimen cup which is selectively removable from an opening in said specimen cup for placing a specimen in said specimen cup through said opening, and which can then be, once again, placed on said specimen cup for closing said opening, said removable lid including an outer partition and an inner partition at said opening for defining a test space with a chemical test strip therein, said outer partition having a transparent portion for allowing a user to see into the test space and said inner partition having an opening means for allowing test fluid to be transferred from a specimen cup on which said lid is placed into said test space; wherein said lid further includes a selectively removable protective cover for selectively covering and uncovering an outer surface of said transparent portion of said outer partition, said protective cover being formed as one piece with said inner partition and being attached thereto along one edge by an integral living hinge, and said selectively removable protective cover being of a size and shape for completely covering substantially all of that portion of the lid to which the protective cover is attached by said living hinge which closes said opening so that when the removable lid is on said specimen cup for closing said opening and said protective cover is covering the outer surface of the transparent portion, it will appear that the protective cover is covering the opening and that one can remove the removable lid by lifting the protective cover from the analytical specimen cup.

2. A removable lid as in claim 1 wherein is further included a color analysis chart mounted on an inside surface of the protective cover, said color analysis chart including colors corresponding to colors achieved by said chemical test strip when it is brought into contact with said specimen to indicate presence of substances in said specimen, whereby a technician can compare the colors of the color analysis chart with the colors of the chemical test strip for reading the chemical test strip.

3. A removable lid as in claim 2 wherein said color-analysis chart extends across said integral hinge.

4. A removable lid as in claim 2 wherein said color analysis chart is formed as a removable label which can be easily removed from said inside surface of the protective cover.

* * * * *